(12) United States Patent
Wiebus et al.

(10) Patent No.: US 6,863,872 B2
(45) Date of Patent: Mar. 8, 2005

(54) METHOD FOR RECOVERING RHODIUM FROM HYDROFORMYLATION PRODUCTS

(75) Inventors: Ernst Wiebus, Oberhausen (DE); Kurt Schalapski, Oberhausen (DE); Michael Mertl, Oberhausen (DE); Richard Fischer, Louisville, KY (US); Rainer Lukas, Essen (DE)

(73) Assignee: Celanese Chemicals Europe GmbH (DE)

( * ) Notice: Subject to any disclaimer, the term of this patent is extended or adjusted under 35 U.S.C. 154(b) by 338 days.

(21) Appl. No.: 10/239,096

(22) PCT Filed: Mar. 14, 2001

(86) PCT No.: PCT/EP01/02848

§ 371 (c)(1),
(2), (4) Date: Sep. 17, 2002

(87) PCT Pub. No.: WO01/72679

PCT Pub. Date: Oct. 4, 2001

(65) Prior Publication Data

US 2003/0049188 A1 Mar. 13, 2003

(30) Foreign Application Priority Data

Mar. 24, 2000 (DE) ......................................... 100 14 844

(51) Int. Cl.$^7$ .............................................. C22B 11/00
(52) U.S. Cl. ......................................................... 423/22
(58) Field of Search ........................... 423/22; 568/451, 568/454, 909

(56) References Cited

U.S. PATENT DOCUMENTS

| 3,716,626 A | * | 2/1973 | Kniese et al. ............... 423/418 |
| 4,131,640 A | * | 12/1978 | von Kutepow et al. ....... 423/22 |
| 4,388,279 A | | 6/1983 | Quick |

FOREIGN PATENT DOCUMENTS

| DE | 1954815 | 5/1971 |
| DE | 2262852 | 7/1973 |
| DE | 2311388 | 9/1974 |
| JP | 63162044 | 7/1988 |
| JP | 63197543 | 8/1988 |
| JP | 03253522 | 11/1991 |

* cited by examiner

*Primary Examiner*—Steven Bos
(74) *Attorney, Agent, or Firm*—Muserlian, Lucas and Mercanti

(57) ABSTRACT

According to the invention, rhodium is recovered from hydroformylation products (feed material) by thermally processing the feed material in the presence of an adsorbent and, optionally, with the additional action of hydrogen.

14 Claims, No Drawings ated mixtures between room temperature and 100° C. and in a pressure range from atmospheric up to 7 MPa. The nitrogen-containing compounds employed for the extraction are ammonia, ammonium hydroxide and amines.

METHOD FOR RECOVERING RHODIUM FROM HYDROFORMYLATION PRODUCTS

This application is a 371 of PCT/EP01/02848 filed Mar. 14, 2001.

The present invention relates to an improved process for recovering rhodium from the products of hydroformylation (oxo process).

The preparation of aldehydes and alcohols by catalytic addition of carbon monoxide and hydrogen onto olefinic double bonds is known. Modern processes make use of metallic rhodium or rhodium compounds as catalysts, which are employed on their own or together with complex-forming ligands, e.g. organic phosphines or esters of phosphorous acid. Skilled workers agree in taking the view that hydridocarbonyl compounds of rhodium which can be represented by the general formula $H[Rh(CO)_{4-x}L_x]$ where L is a ligand and x is 0 or an integer from 1 to 3 are active as catalyst under the reaction conditions.

The use of rhodium catalysts has a number of advantages over the classical oxo process with cobalt catalysts. The activity of rhodium catalysts is higher than that of cobalt catalysts, and terminal olefins are converted into unbranched aldehydes to a greater extent in the presence of rhodium (in the form of rhodium complex compounds) than in the presence of cobalt. In addition, production plants can be operated substantially without problems on use of rhodium catalysts, which relates in particular to the carrying out of the synthesis and the discharge of the products.

A factor which determines the economics of the rhodium process is that the losses on removal and recovery of the noble metal are minimized, irrespective of whether it was employed with or without additional complexing agent as catalyst. After completion of the reaction, the rhodium is dissolved as carbonyl compound, which also contains, if appropriate, other ligands, in the hydroformylation product.

For workup, the crude product of the synthesis is initially decompressed in one or more stages to atmospheric pressure to release dissolved synthesis gases. The rhodium is removed either directly from the decompressed crude product or from the residue left after removal of the aldehydes from the crude product by distillation. The second variant is applied when the rhodium catalyst contains not only carbon monoxide but also other ligands, e.g. phosphines or phosphites, in complex linkage. It can also be used when the hydroformylation was carried out with rhodium alone and, during the further treatment of the reaction product by distillation, care is taken that rhodium does not escape in the form of volatile compounds from the distilled material or the distillation residue.

Irrespective of the chosen form of processing the reaction mixture, account must be taken of the fact that the noble metal is present in the crude product and in the distillation residue in a concentration of only a few ppm, and thus removal must therefore be carried out with great care.

In these circumstances, it is not surprising that the recovery of rhodium from the products of the oxo process, including the distillation residues therefrom, has been investigated many times. The work has led to the development of numerous processes, and a few of them have also been applied on the industrial scale.

In a process described in U.S. Pat. No. 4,292,196, metals of group 8 of the Periodic Table which are present as catalysts in the form of metal carbonyls or organometallic compounds homogeneously dissolved in hydroformylation products are extracted with water-soluble, nitrogen-containing compounds. The removal takes place at temperatures between room temperature and 100° C. and in a pressure range from atmospheric up to 7 MPa. The nitrogen-containing compounds employed for the extraction are ammonia, ammonium hydroxide and amines.

Another process for removing rhodium from the products of the oxo process, which is based on extraction with a complex-forming reagent, is described in EP 0 147 824 B1. The extractants employed are water-soluble sulfonates or carboxylates of organic phosphines in the form of an aqueous solution which is immiscible with the crude oxo product.

In both processes, the metal carbonyl or organometallic compounds present in the hydroformylation products are treated with the extractant without previous cleavage of the coordinate or metal-carbon linkages.

When the known processes are carried out industrially they allow up to 90% of the originally employed rhodium to be recovered, and the remainder of the noble metal is lost. Problems occasionally arise in the processing of the rhodium extracts owing to the fact that the rhodium concentration in the aqueous solutions is lower and either large liquid volumes must be treated or the solutions must previously be concentrated. Further difficulties may emerge on reuse of the rhodium which has been recovered as metal or as compound. This is why there is interest in perfecting the removal even of small residues of rhodium from the products of the oxo process, in further reducing the losses of rhodium, and in obtaining the metal in a form which allows it to be converted back into the catalyst without difficulty.

The invention achieves the object described above by a process for recovering rhodium which is present in the products of the hydroformylation of olefinically unsaturated compounds. It comprises heating the hydroformylation products in the presence of a solid adsorbent to temperatures of from 50 to 200° C.

Surprisingly, it is possible with the novel process to isolate rhodium from the reaction mixture even if present therein as compound dissolved in very low concentration. The claimed procedure ensures that a very high proportion of the rhodium is removed. Of particular importance in this connection is that the thermal treatment of the starting material takes place at moderate temperatures. Unwanted side reactions are therefore not a worry.

The starting material comprises the products of the hydroformylation of olefinically unsaturated compounds. By this term is meant both aldehydes and polyfunctional compounds containing aldehyde groups, as well as secondary products of these original reaction products (primary products). The secondary products include, in particular, compounds of higher molecular weight which have been produced from the aldehydes by aldol condensation and may also, in a subsequent reaction, eliminate water to form unsaturated compounds. They are present especially in the residues remaining in the bottom product after removal of the aldehydes by distillation. The secondary products also include alcohols which are produced by hydrogenation of the aldehydes and, by appropriate management of the reaction in special cases, also represent the intended main product of the hydroformylation reaction. The novel process is principally aimed at recovering rhodium from the hydroformylation of olefins having 2 to 12 carbon atoms, in accordance with the economic importance of the aldehydes prepared from them. Besides aldehydes, the saturated and unsaturated condensation products and alcohols, the mixtures to be processed may also contain solvents.

Rhodium is present in the hydroformylation products as carbonyl or hydridocarbonyl compounds. The process of the invention allows reaction mixtures which contain rhodium in very wide concentration ranges to be treated. It is applied successfully both with concentrations of 0.5 ppm by weight rhodium and with concentrations of 500 ppm by weight rhodium, based on the starting material.

Application of the novel process is not confined to mixtures which contain rhodium only as carbonyls. On the contrary, it is also possible to employ products of the oxo process prepared by employing rhodium complex compounds which contain other ligands in addition to carbon monoxide. These ligands include in particular, compounds of trivalent phosphorus such as phosphines and phosphites, which have free electron pairs and are therefore able to form coordination compounds with the noble metal. However, before treating such products by the process of the invention, it is necessary to convert these ligands into compounds which do not form complexes with rhodium. In a proven procedure, for this purpose the phosphorus(III) compounds are converted by oxidation to phosphorus(V) compounds According to the invention, the products of the oxo process are thermally treated, i.e. heated to 50 to 200° C., in the presence of an adsorbent, so that the rhodium which is present in bound form, but also to a minor extent where appropriate as fine metal particles, is deposited out of the reaction mixture. Although temperatures lower than 50° C. are not precluded, they often prove to be unsuitable, inter alia for economic reasons, because of the low rate of reaction (deposition). Higher temperatures only rarely result in an improvement in the rate of deposition. However, they may distinctly reduce the yield of the target compounds, principally aldehydes, through the occurrence of subsequent reactions leading, for example, to the formation of unwanted condensation products. It has proved particularly suitable to carry out the thermal treatment of the hydroformylation products at 70 to 150° C.

The term adsorbent means solid substances which are able, because of their large surface area, to take up and accumulate rhodium compounds present in dissolved form and, as already stated, also fine metal particles. The accumulation takes place substantially selectively, i.e. rhodium compounds are preferentially bound by the surface forces of the adsorbent, whereas the concomitant organic substances, which are present in large excess, are immobilized by the adsorbent to only a minor extent, if at all.

Suitable adsorbents are the materials familiar in the practice of chemistry, both in the laboratory and in industrial plants, especially activated carbon, by surface-area polysilicic acids such as silica gels (silica xerogels), highly disperse silica (which is marketed, for example, under the brandname Aerosil® and high surface-area aluminum oxides and aluminum oxide hydrates. Which of said adsorbents is employed in the individual case depends on the form in which the rhodium is to be recovered. If recovery as compound is the priority, then silicon- and aluminum-based adsorbents will generally be preferred, because they are resistant even to treatment with aggressive chemicals to remove the rhodium and therefore can be employed repeatedly.

The adsorbents can be employed in the novel process as single substances or as mixtures of different substances. This makes it possible to adapt the process of the invention to individual requirements and also to solve specific problems. In general, mixtures used will be of adsorbents which differ only in physical behavior, e.g. in the surface properties, but whose chemical structure is the same or similar. This ensures inter alia that the substance mixtures loaded with the novel metal can be processed without difficulty to adsorbent and metal.

Recovery of rhodium in metallic or oxidic form is particularly simple on use of activated carbon. In this case, the activated carbon loaded with rhodium is combusted and the noble metal remains behind, finely dispersed, in elemental form or as oxide. It can be directly converted into the catalyst, in a separate reaction step or in the reaction mixture itself.

In a preferred embodiment of the procedure of the invention, thermal treatment of the rhodium-containing hydroformylation products is carried out not only in the presence of an adsorbent but also in the presence of hydrogen. The hydrogen is employed in excess relative to rhodium, in pure form or mixed with inert gases; the use of pure hydrogen is generally preferred. The amount of hydrogen may be varied within wide limits.

It is advisable to use 100 to 2000, in particular 300 to 1200, mol of hydrogen per mol of rhodium. It is particularly noteworthy that the aldehydes present in the reaction mixture are not hydrogenated by the thermal treatment of the hydroformylation products in the presence of hydrogen. This is because this reaction will not be precluded owing to the formation of catalytically active metallic rhodium.

The novel process can be carried out both under atmospheric pressure and under pressures of up to 15 MPa. Pressures in the range from 5 to 10 MPa have proved particularly suitable.

To carry out the rhodium removal by the process of the invention in practice, the rhodium-containing mixture is brought into contact with the adsorbent and, where appropriate, with hydrogen in a suitable reactor. The adsorbent can, for example, be arranged as fixed bed in a tubular reactor through which the rhodium-containing phase flows. The volume of the fixed bed and the size of the adsorbent particles may be varied within wide limits and thus adapted to the chosen reaction conditions and the circumstances of the process, such as the desired flow rate. It has proved suitable to maintain a space velocity in the range from 0.1 to 2.5, in particular from 1.0 to 1.5 ($V_{react.\ mixt.}/[V_{adsorbent} \cdot h]$).

In another embodiment of the procedure of the invention, the adsorbent, which in this case can be very fine-particle, is suspended in the rhodium-containing medium. It is expedient to agitate the suspension continuously, e.g. by stirring or introducing a gas such as hydrogen, in order to achieve intimate contact between the liquid phase and the adsorbent. The mass ratio of liquid phase to adsorbent can be set substantially without restrictions and thus appropriate for individual requirements. It has proved suitable to employ 1 to 5, preferably 1.5 to 3.5, parts by weight of adsorbent per 100 parts by weight of rhodium-containing mixture. This process variant is suitably implemented in, for example, stirred vessels or autoclaves.

The reaction time depends on the rhodium concentration in the starting material. It is also determined by the amount of hydrogen employed and by the reaction temperature and pressure. Under identical reaction conditions, higher rhodium concentrations require longer treatment times than do lower concentrations. Rhodium deposition on the adsorbent is promoted by a large hydrogen supply and high temperatures and pressures. In most cases, a single thermal treatment of the starting mixture is sufficient. This applies equally to the reactions carried out in the presence and in the absence of hydrogen. It is, of course, possible to recirculate the starting mixture in order to complete the removal of rhodium by multiple treatment of the organic phase. It is likewise possible to carry out the adsorption in a plurality of stages. The reaction can be carried out both batchwise and continuously.

The novel process has proved to be excellent for depositing rhodium present dissolved as compound in hydroformylation products. Apart from the simplicity of its industrial implementation, it is particularly noteworthy that it allows mixtures containing rhodium in very wide concentration ranges to be employed. It is applied successfully with concentrations both of 0.5 ppm by weight and of 500 ppm by weight rhodium in the starting material. It has proved particularly suitable for treating hydroformylation mixtures in which rhodium is present in concentrations of from 2.5 to 250 ppm by weight. Depending on the nature of the starting material and chosen reaction conditions, on application of the claimed procedure it is possible to deposit up to about 98% of the rhodium on the adsorbent and reduce the rhodium concentration in the treated substrate to below 0.1 ppm by weight.

The process of the invention is described in detail in the following examples. It is, of course, not confined to the embodiments described.

EXAMPLES

Example 1

The deposition of the rhodium onto the adsorbent takes place in a tubular reactor at 60° C. under a pressure of 7 MPa in the presence of hydrogen. The reaction mixture employed had not been pretreated (i.e. had merely been decompressed) and had a rhodium content of 4.2 ppm by weight, and had been obtained from the hydroformylation of butene using rhodium as catalyst. The starting mixture was introduced at the top of the reactor. It flowed with a space velocity of 1.5 V/[V·h] through granular activated carbon of the NORIT brand, type GAC 830 plus, as adsorbent, which was disposed on a porous plate at the foot of the reactor. The rhodium content remaining in the treated product after a single passage through activated carbon was 0.08 ppm by weight, corresponding to a deposition rate of 98%.

Example 2

This test was carried out in the apparatus and under the reaction conditions (temperature, pressure, presence of hydrogen, space velocity) of example 1. The reaction mixture employed had not been pretreated and had a rhodium content of 2.82 ppm by weight, and had been obtained by hydroformylation of octene using rhodium as catalyst. The adsorbent was once again activated carbon of the NORIT brand, type GAC 830 plus. The rhodium content remaining in the treated product after a single passage through activated carbon was 0.099 ppm by weight, corresponding to a deposition rate of 96.5%.

Example 3

This test was carried out in the apparatus of example 1 at 80° C., under atmospheric pressure in the absence of hydrogen. The reaction mixture employed had not been pretreated and had a rhodium content of 1.94 ppm by weight, and had been obtained by hydroformylation of octene. The space velocity and adsorbent corresponded to those in examples 1 and 2. The rhodium content remaining in the treated product after a single passage through activated carbon was 0.21 ppm by weight, corresponding to a deposition rate of 89.2%.

Example 4

The deposition of the rhodium onto the adsorbent took place in a stirred autoclave at 80° C. under a pressure of 7 PMa in the presence of hydrogen. The 500 g of reaction mixture employed had not been pretreated, had been obtained by hydroformylation of octene using rhodium as catalyst and contained 2.21 ppm by weight rhodium. 12.5 g of activated carbon (i.e. 2.5% based on the mixture) of the NORIT brand, type GAC 830 plus, in powder form were suspended in this mixture. The product obtained after a treatment time of 2 h still comprised 0.27 ppm by weight rhodium, corresponding to a deposition rate of 88%.

What is claimed is:

1. A process for recovering rhodium present in the aldehyde—or aldehyde group-containing polyfunctional compounds of the decompressed crude products of the hydroformylation of olefinically unsaturated compounds, which comprises heating the hydroformylation products in the presence of activated carbon, high surface-area polysilicic acid, high surface-area aluminum oxide or high surface-area aluminum oxide hydrate as solid adsorbent and in the presence of hydrogen under pressures of from 0.1 to 15 MPa to temperatures of from 50 to 200° C.

2. The process as claimed in claim 1, wherein the hydroformylation products are heated to temperatures of from 70 to 150° C.

3. The process as claimed in claim 1, wherein the hydrogen is employed in pure form or mixed with inert gases.

4. The process as claimed in claim 1, wherein hydrogen is employed in at least stoichiometric amount relative to rhodium.

5. The process as claimed in claim 1, wherein from 100 to 2000 mol of hydrogen are used per mol of rhodium.

6. The process as claimed in claim 1, wherein the heating of the hydroformylation products is carried out under pressures of from 5 to 10 MPa.

7. The process as claimed in claim 1, wherein the heating of the hydroformylation products takes place on an adsorbent disposed as fixed bad.

8. The process as claimed in claim 7, wherein space velocities of from 0.10 to 2.5 $V_{react\ mixt.}/V_{adsorbent}\cdot h$] are maintained in the heating of the hydroformylation products.

9. The process as claimed in claim 1, wherein the adsorbent is suspended in the hydroformylation product.

10. The process as claimed in claim 9, wherein from 1 to 5 parts by weight of adsorbent are suspended per 100 parts by weight of rhodium-containing hydroformylation product.

11. The process of claim 3 wherein the hydrogen is used in pure form.

12. The process of claim 5 wherein the amount of hydrogen used is 300 to 1200 mole.

13. The process of claim 8 wherein the space velocities are 1.0 to 1.5.

14. The process of claim 10 wherein 1.5 to 3.5 parts by weight of adsorbent are suspended.

* * * * *